(12) United States Patent
Das

(10) Patent No.: US 8,430,934 B2
(45) Date of Patent: Apr. 30, 2013

(54) VASCULAR OCCLUSION DEVICE

(75) Inventor: Gladwin S. Das, Arden Hills, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 1841 days.

(21) Appl. No.: 10/931,937

(22) Filed: Sep. 1, 2004

(65) Prior Publication Data

US 2005/0070957 A1    Mar. 31, 2005

Related U.S. Application Data

(63) Continuation of application No. PCT/US03/06473, filed on Mar. 3, 2003.

(60) Provisional application No. 60/361,122, filed on Mar. 1, 2002.

(51) Int. Cl.
*A61F 2/02* (2006.01)
(52) U.S. Cl. .................................................. 623/23.72
(58) Field of Classification Search .......... 606/213, 606/215, 232; 623/23.7, 23.72; 600/31, 600/32; 604/41, 42
See application file for complete search history.

(56) References Cited

U.S. PATENT DOCUMENTS

| 5,254,133 | A | * | 10/1993 | Seid .............................. 606/215 |
| 5,312,435 | A | | 5/1994 | Nash et al. ..................... 606/213 |
| 5,342,393 | A | * | 8/1994 | Stack ............................. 606/213 |
| 5,350,399 | A | | 9/1994 | Erlebacher et al. ........... 606/213 |
| 5,827,325 | A | | 10/1998 | Landgrebe et al. ........... 606/213 |
| 5,904,703 | A | | 5/1999 | Gilson ........................... 606/213 |
| 6,214,029 | B1 | * | 4/2001 | Thill et al. ..................... 606/213 |
| 6,281,262 | B1 | * | 8/2001 | Shikinami ..................... 523/105 |
| 6,312,446 | B1 | | 11/2001 | Huebsch et al. .............. 606/213 |
| 6,458,153 | B1 | * | 10/2002 | Bailey et al. ................. 623/1.24 |
| 6,623,492 | B1 | * | 9/2003 | Berube et al. ................. 606/151 |
| 6,949,116 | B2 | * | 9/2005 | Solymar et al. .............. 623/1.12 |
| 2002/0183787 | A1 | * | 12/2002 | Wahr et al. .................... 606/213 |
| 2004/0267306 | A1 | * | 12/2004 | Blaeser et al. ................ 606/213 |

FOREIGN PATENT DOCUMENTS

| CA | 1045304 | 1/1979 |
| GB | 2269321 | 2/1994 |
| JP | 51115088 | 10/1976 |
| WO | WO-96/32882 | 10/1996 |
| WO | WO-9632882 A1 | 10/1996 |
| WO | WO-01/17435 | 3/2001 |

OTHER PUBLICATIONS 2003-572469, "Application Serial No. 2003-572469 Office Action mailed on Mar. 3, 2009", 2.
"Canadian Application No. 2,477,833 ,Notice of Allowance Mailed on Oct. 14, 2010", 1 Pg.
"Canadian Application Serial No. 2,477,833, Office Action Response Filed Jul. 28, 2010", Office Action Response Filed, 5.

* cited by examiner

*Primary Examiner* — Ryan Severson
*Assistant Examiner* — Jonathan W Miles
(74) *Attorney, Agent, or Firm* — Schwegman, Lundberg & Woessner, P.A.

(57) ABSTRACT

An occlusion device includes a pair of connected members configured for being situated on opposing sides of a hole in a tissue, wherein the pair of connected members are formed of a material which is bioadsorbable to the tissue. The pair of connected members can include a non-metallic skeleton.

22 Claims, 17 Drawing Sheets

US 8,430,934 B2

VASCULAR OCCLUSION DEVICE

Related Application

This application is a U.S. Continuation Application based off PCT Application No. PCT/US03/06473, filed Mar. 3, 2003 and Published as WO 03/073944 on Sep. 12, 2003, which application claims the benefit of U.S. Provisional Application, Ser. No. 60/361,122, filed Mar. 1, 2002, under 35 USC119(e), both which are incorporated herein by reference in their entireties.

FIELD OF THE INVENTION

This invention relates to the field of medical devices, and more specifically to an apparatus for vascular occlusion.

BACKGROUND

Vascular occlusion devices such as atrial septal defect closure devices are used for closing defects or holes in the vascular system of a body. Such devices usually include an occluding member which is dimensioned larger than the hole, and some technique for mounting the occluding member to the tissue proximate the defect or hole.

The devices are typically made of a wire frame or skeleton which can become fatigued or perforate the tissue wall. It is also desirable to center the device within the hole and provide a stable technique for keeping the device securely mounted to the tissue.

DETAILED DESCRIPTION

Figure 1A:
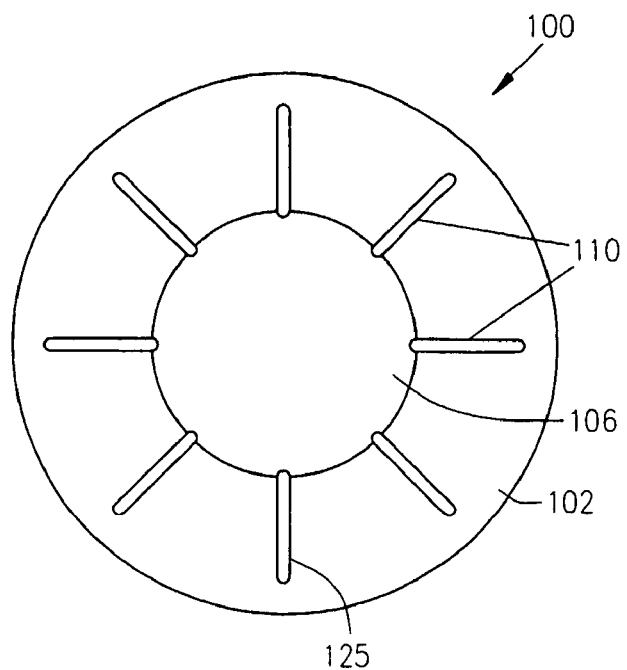
FIG. 1A shows a front view of a vascular occlusion device according to one embodiment.
Figure 1B:
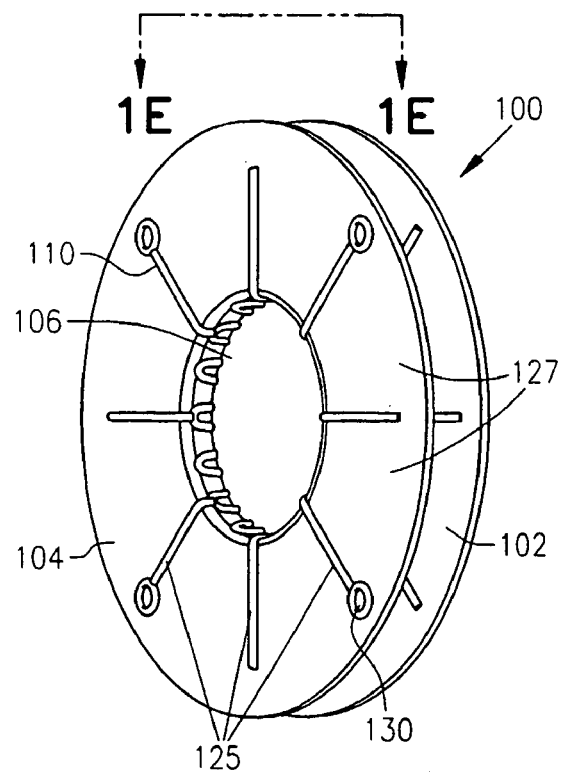
FIG. 1B shows a perspective view of the vascular occlusion device of FIG. 1A.
Figure 1C:
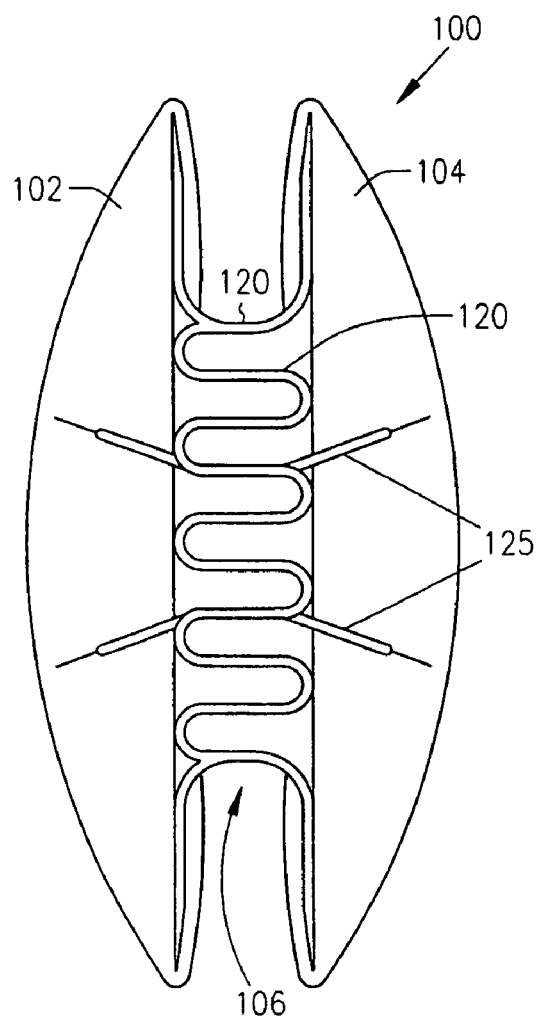
FIG. 1C shows a side view of the vascular occlusion device of FIG. 1A with the flanges folded outward.
Figure 1D:
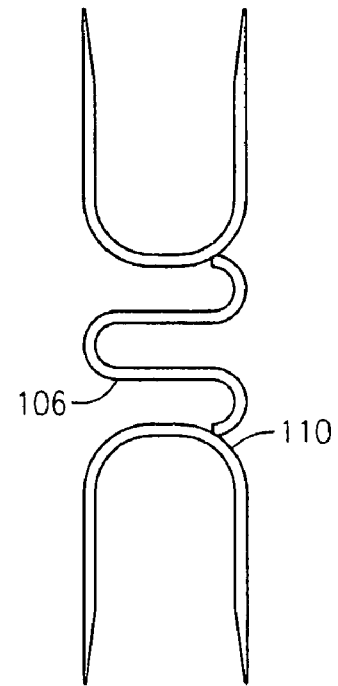
FIG. 1D shows side view of the vascular occlusion device of FIG. 1A.
Figure 1E:
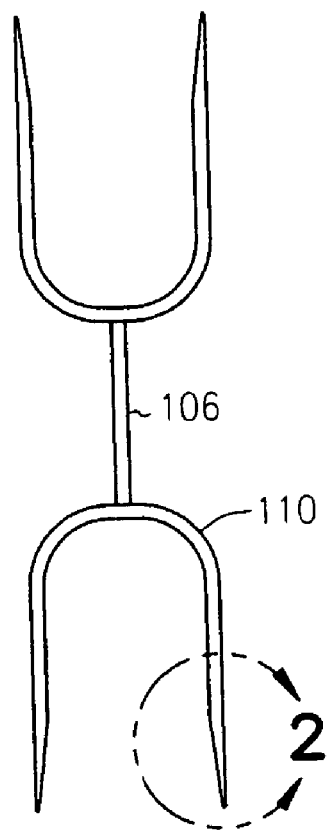
FIG. 1E shows a side section view along line E-E of FIG. 1B.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

The present system provides a device that can be used to occlude defects in the vascular system by minimally invasive means. Patients are often born with congenital defects in the heart commonly alluded to as "holes in the heart." This may be between the upper chambers in the heart called "atrial septal defects" or between the lower chambers of the heart called "ventricular septal defects." In other instances, it may be "patent ductus arteriosii" when it is a communication between the aorta and pulmonary artery. In addition, there may be arterio-venous fistulae at several sites within the body, or the presence of collateral arteries to the lungs that bring excessive amounts of blood and require closure.

In recent years, after diagnostic or therapeutic cardiac catheterization, it has become possible to close the arterial puncture site with devices, and because of the anticoagulation they receive, the potential for bleeding and prolonged bed rest can be avoided. However the devices for the closure of heart defects or femoral hemostatic devices have clinical problems and there is a need for a more optimal method of closure.

In the case of cardiac septal defects, some present devices are made of metallic frameworks with single or multiple metallic wires in different geometries. These have the potential of erosion into surrounding structures and corrosion as these implants in children will remain in place for 70 years and more. Some self-centering devices have decreased the potential for residual leaks and permit the almost complete occlusion of these defects. However some of these devices are bulky, and made of several bulky wires.

In some embodiments, the present system includes a vascular occlusion device that can be self-centering, can completely occlude defects, and can also be retrieved back into the delivery catheter in case of sub-optimal deployments. In one embodiment, a vascular occlusion device can include no metallic components. For example, the device can be made from bio-compatible plastic materials that permit it to be injection molded, vacuum formed, or extruded. This makes the manufacturability of such a device quite simple and large quantities can be manufactured quite easily. In one embodiment, the device is made from a bio-adsorbable polymer or a bio-degradable polymer. After deployment of the device, such a polymer is gradually replaced by fibrous tissue and resorbed over a period of months. No metallic components remain and this permits the most desirable form of repair of such defects. In other instances, where a bio-adsorbable material is not appropriate, for fear of aneurysm formation in high pressure shunts, silicone elastomers, polyurethanes or combinations of the two can be used.

FIG. 1A-7 show a vascular occlusion device 100 according to one embodiment. Device 100 includes a double disk device, with two flanges 102 and 104 that extend outwards from a central area 106. In one embodiment, the central area 106 is dimensioned to act as a self-centering mechanism to allow the flanges and the device to be substantially centered over the defect. The central area occludes the defect and extends to the double flanges circumferentially. In one embodiment, central area 106 has a diameter of approximately 12 mm, with the flanges 102 and 104 having a diameter of approximately 30 mm.

Device 100 includes a self-expanding skeleton structure 110 that provides the major structural strength of the device. Skeleton structure 110 includes a plurality of ribs 125. Between each of the ribs 125 are thinner membrane portions 127. In one example, the membrane portions 127 can be approximately 0.01 inches thick, or less. Ribs 125 can be approximately 0.025 inches thick. Skeleton 110 supports a main body structure which includes the flanges 102 and 104. As seen in FIGS. 1C, 1D, 3, 4, 5, 6 and 7, the skeleton has a sinuous structure around the central rim 120 that permits the rim area to be collapsed down. From this, there are the plurality of spoke-like projections or ribs 125 that permit folding of the flanges. In one example, ribs 125 extend radially along each disk. On one of the disks, one or more holes 130 are incorporated whose function is to be the sites to tether it to the release mechanism (see FIG. 5) with a tether 139. In one embodiment, holes 130 are located at the ends of ribs 125 with a section of rib encircling the hole.

Figure 4:
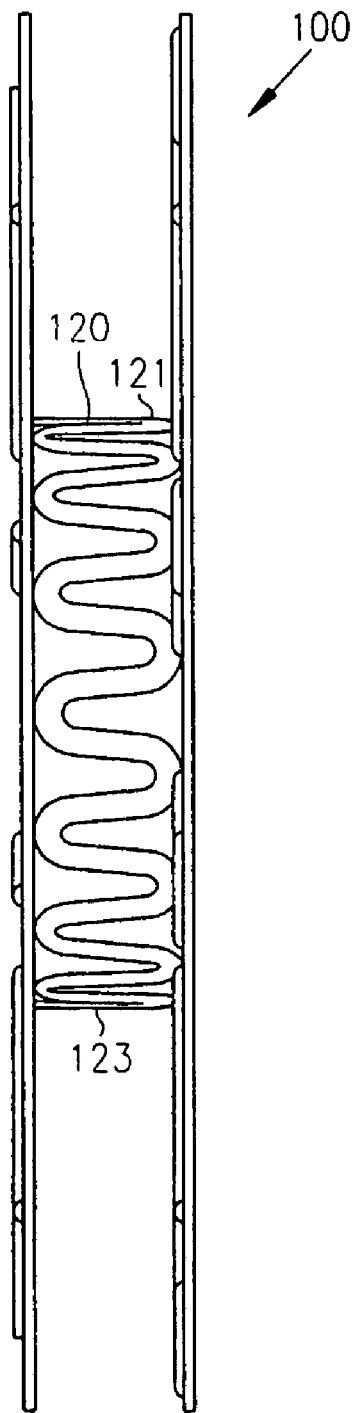
FIG. 4 shows a side view of the vascular occlusion device of FIG. 1A.
Figure 5:
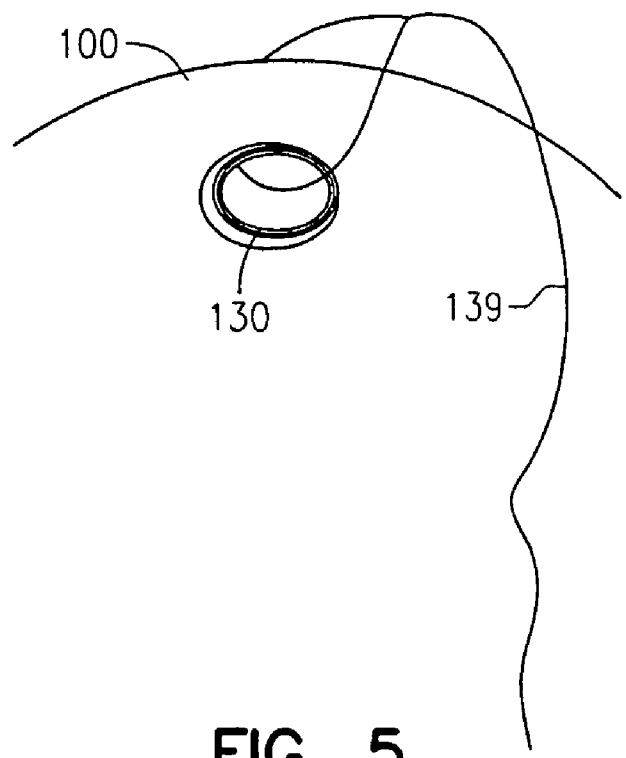
FIG. 5 shows a detail of a front portion of the vascular occlusion device of FIG. 1A.
Figure 6:
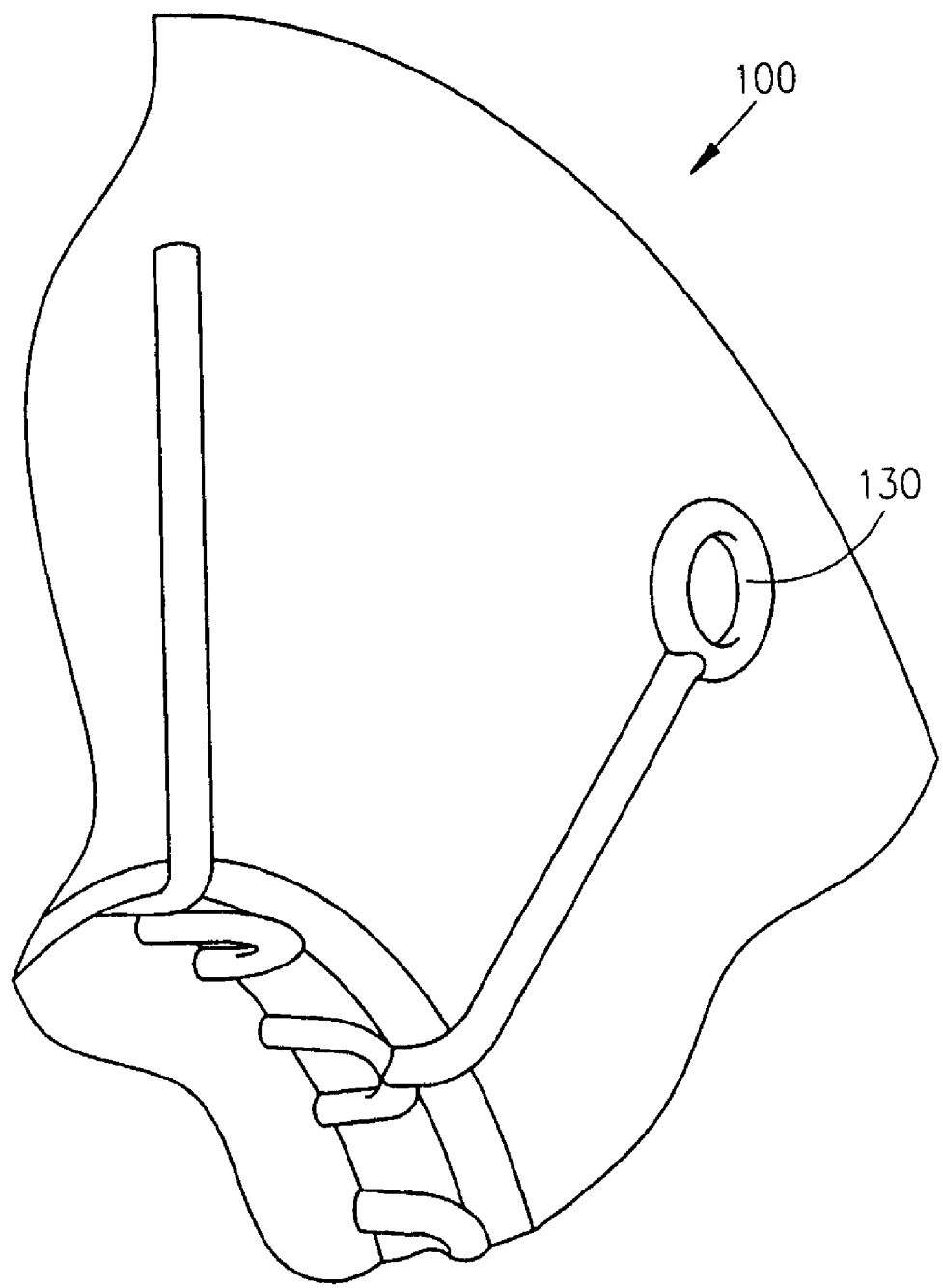
FIG. 6 shows a detail of a front portion of the vascular occlusion device of FIG. 1A.
Figure 7:
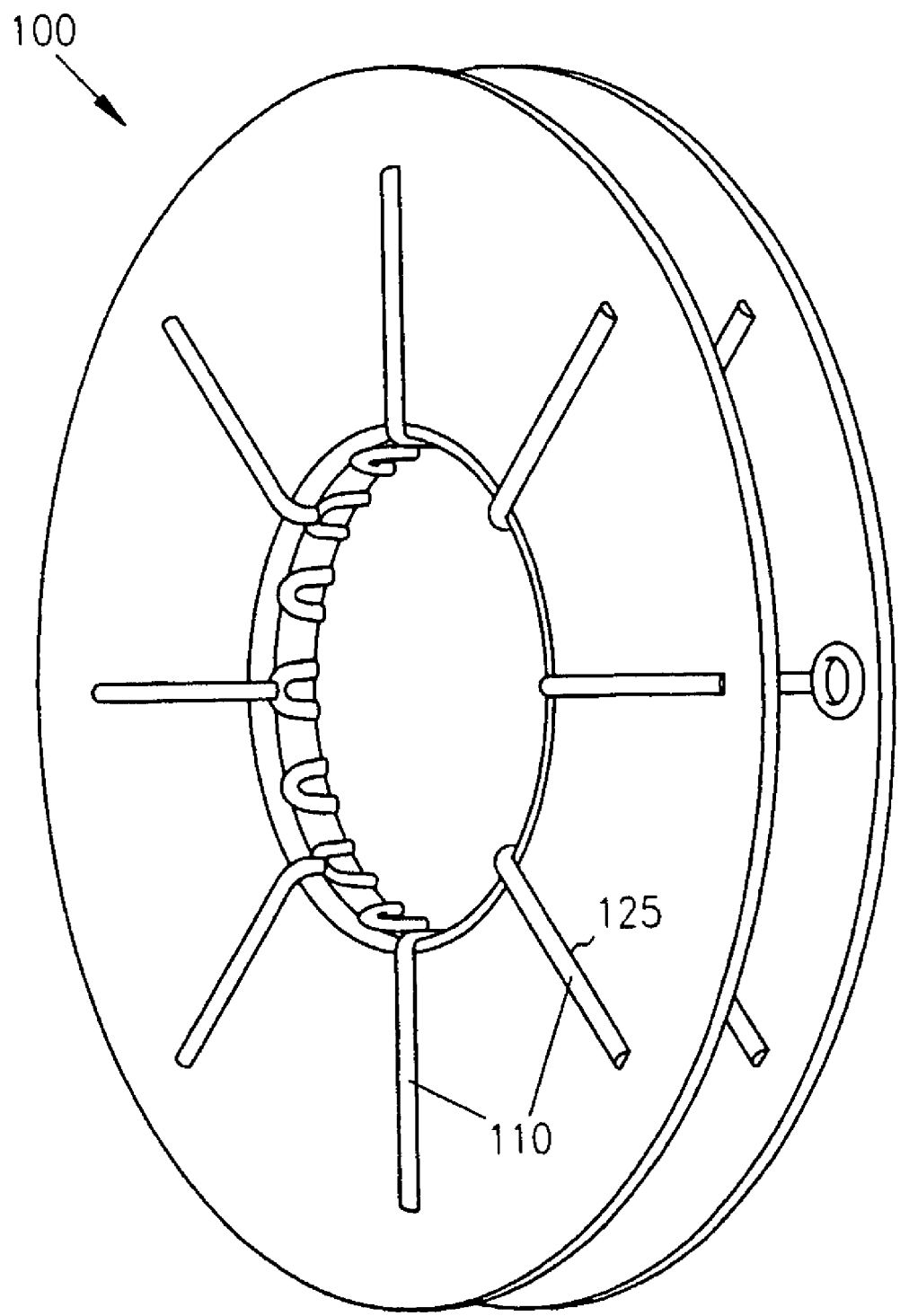
FIG. 7 shows a rear perspective view of the vascular occlusion device of FIG. 1A.
Figure 8A:
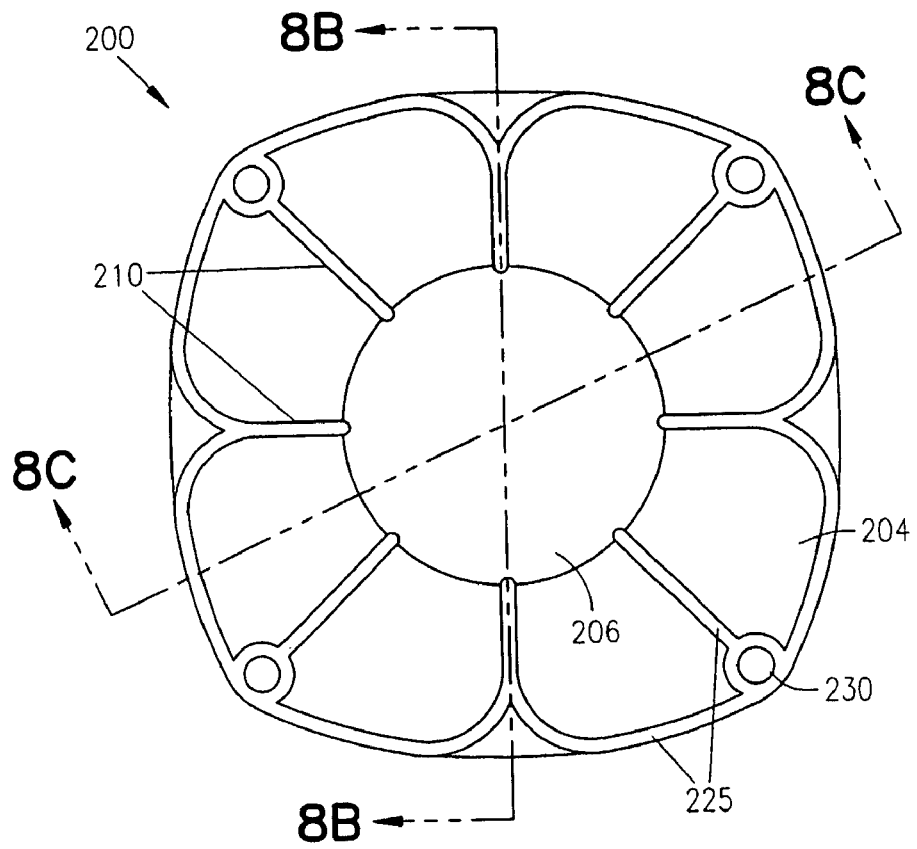
FIG. 8A shows a front view of a vascular occlusion device according to one embodiment.
Figure 8B:
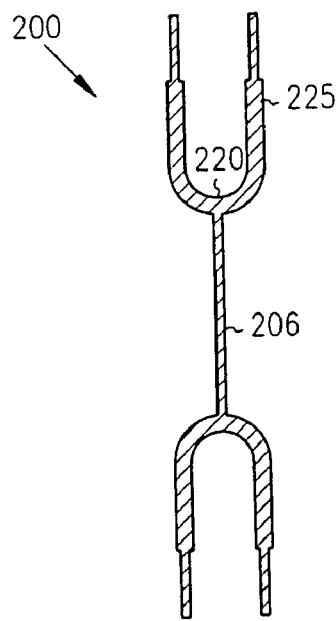
FIG. 8B shows a side sectional view along line B-B of the vascular occlusion device of FIG. 8A.
Figure 8C:
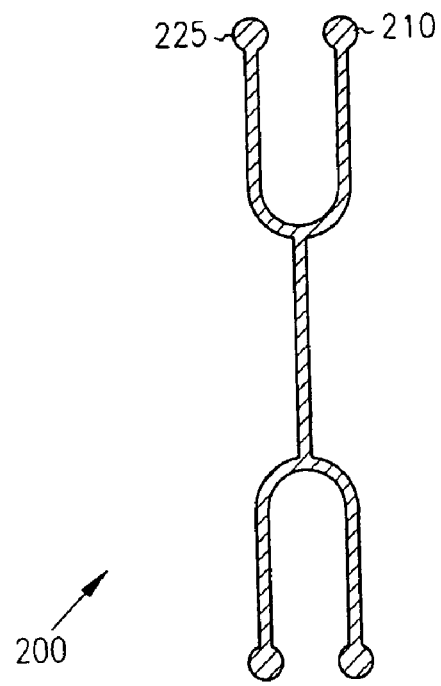
FIG. 8C shows a sectional view along line C-C of FIG. 8A.
Figure 8D:
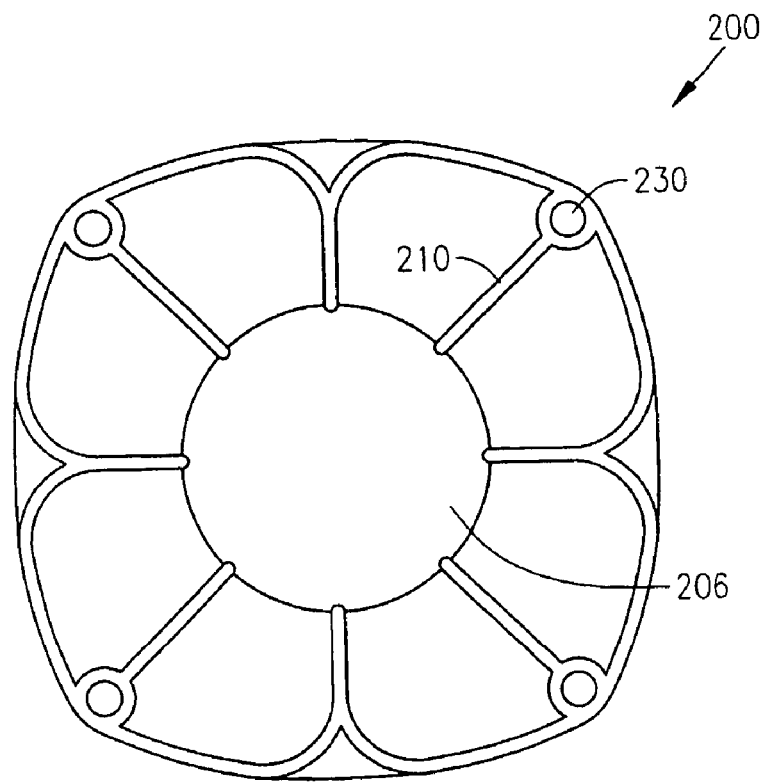
FIG. 8D shows a view of the vascular occlusion device of FIG. 8A.
Figure 8E:
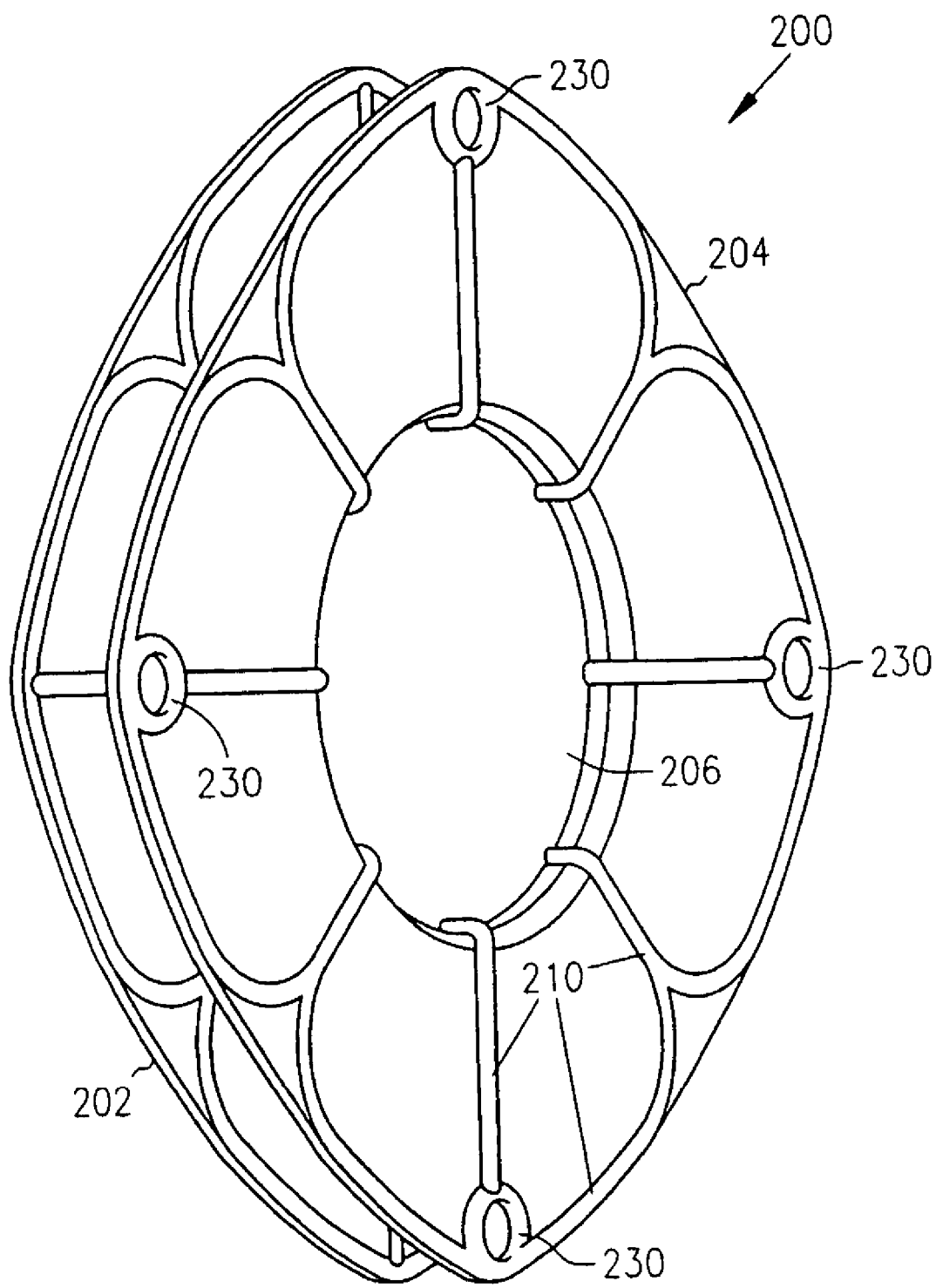
FIG. 8E shows a front perspective view of the vascular occlusion device of FIG. 8A.
Figure 9:
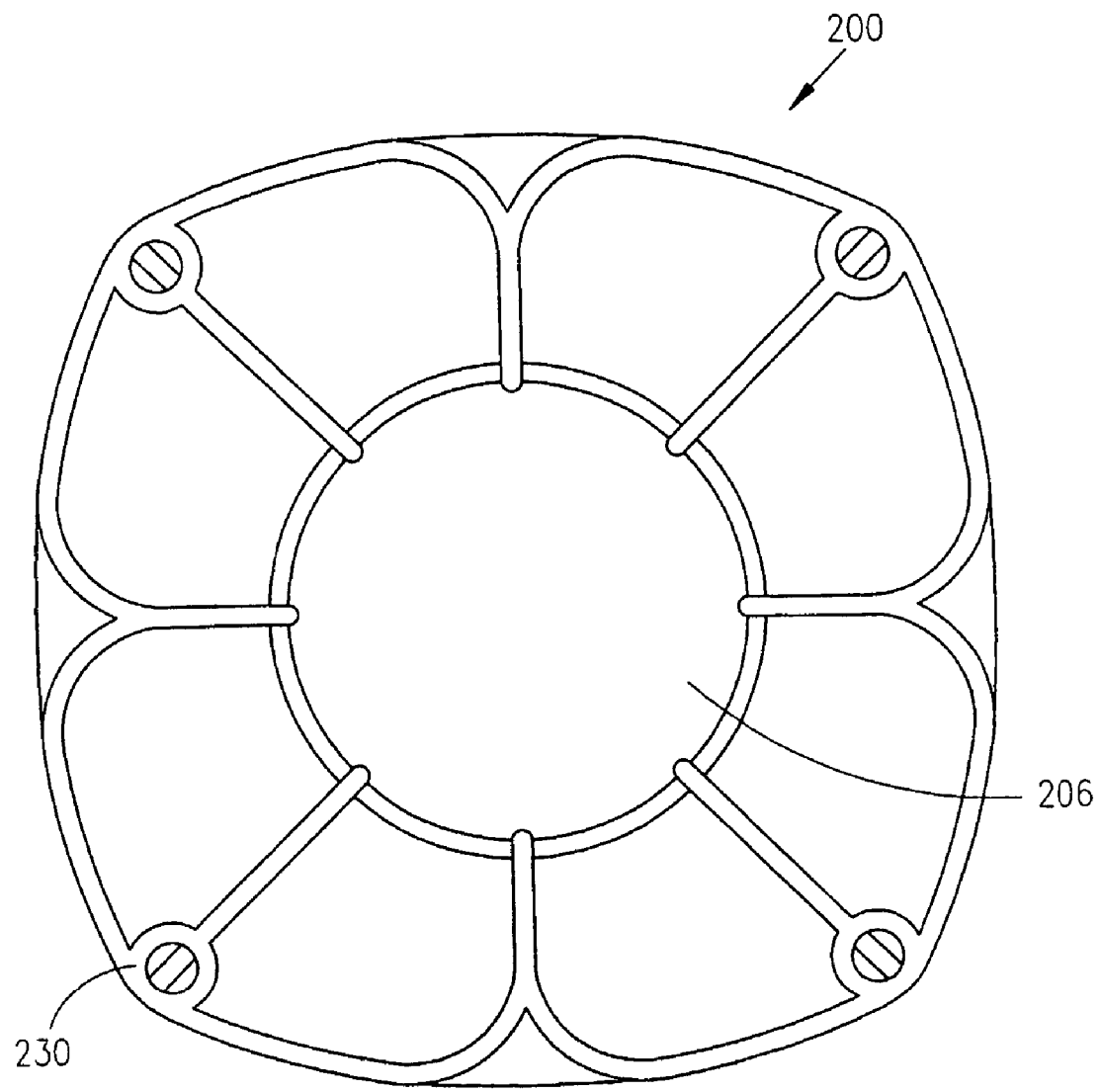
FIG. 9 shows a front view of the vascular occlusion device of FIG. 8A.
Figure 10:
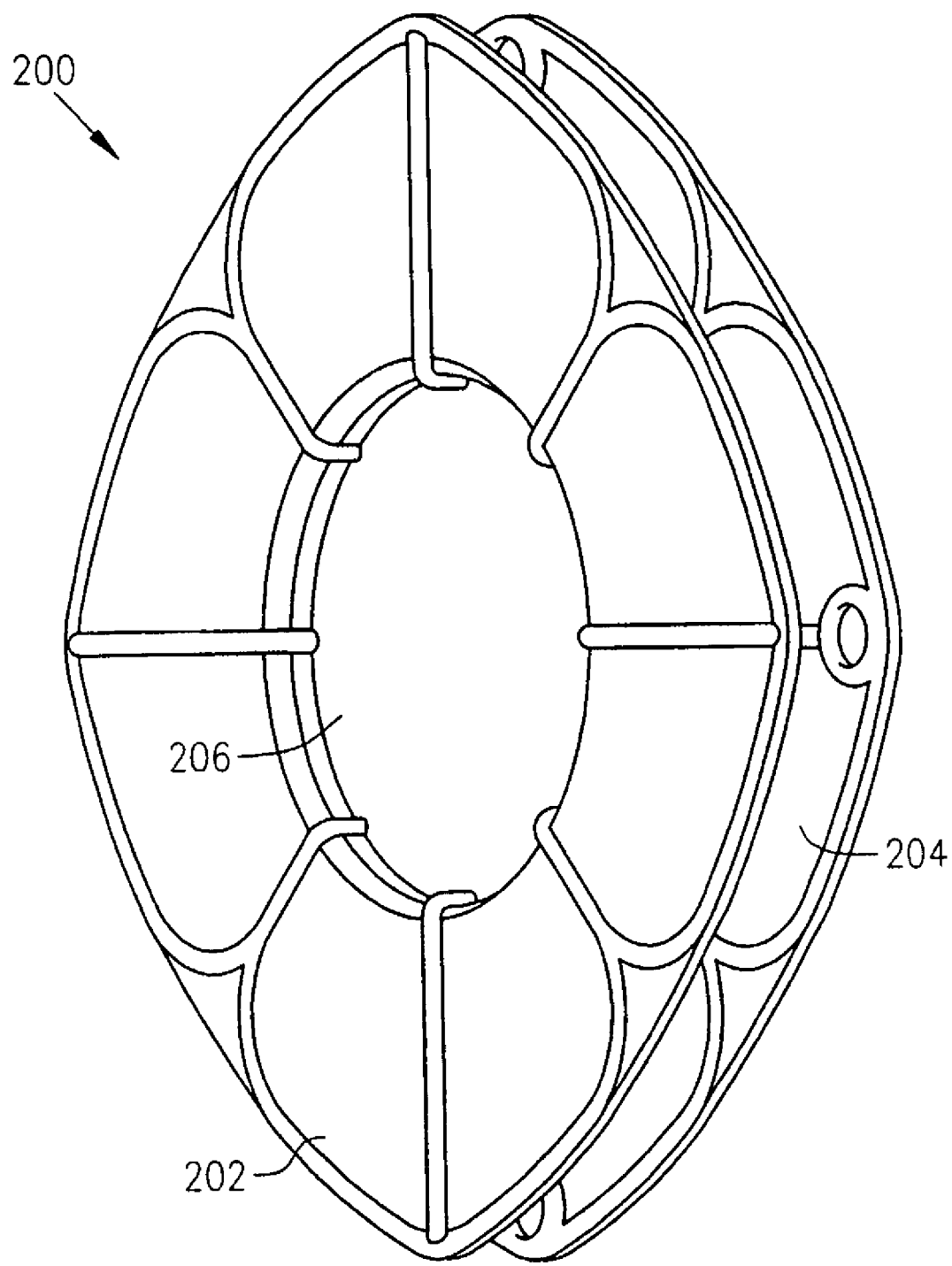
FIG. 10 shows a rear perspective view of the vascular occlusion device of FIG. 8A.

Device 100 is flexible, compressible, and self-expandable and can be used in a manner known in the art. In one example use, the device 100 can be collapsed into a catheter by folding the flanges 102 and 104 outwards and collapsing the central rim 120. The catheter is then passed through an atrial or ventricular septal defect, or other hole in a body. The first disk 102 of device 100 is pushed out of the catheter and springably opens on one side of the defect. The rib configuration of the skeleton structure of each flange automatically expands the flange to its original dimensions on release from the confines of the catheter. The expanded disk 102 is then drawn back to the defect. The catheter is pulled back, and second disk 104 then springably opens on the second side of the defect. The central rim area 120 also expands to its original size and abuts the inner diameter surface of the defect. This acts as a centering mechanism to center the flanges of the device on each side of the defect. Referring to FIG. 4, the outer surface of rim 120 diametrically extends from a first surface 121 to a second surface 123. These surfaces and the rest of the expanded rim surface are biased towards and can contact the inner surface of the defect to help center the device.

Once deployment of the device is considered optimal, the device is released. If deployment is sub-optimal, tethers 139, which are attached at one or more of holes 130 can be used to retrieve the device. By pulling back on the tethers, the device can be re-collapsed into the catheter. Again, holes 130 are structurally connected to ribs 125. Thus, when the tethers are pulled back, the force against the ribs of the skeleton structure force flange 104 to collapse. The device can then be drawn back into the catheter to be re-deployed.

Figure 2:
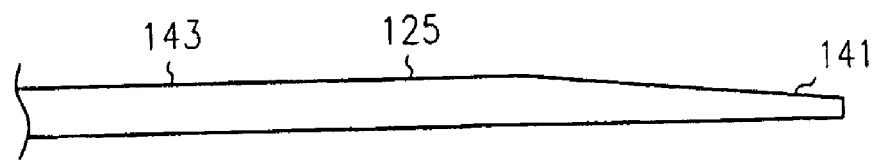
FIG. 2 shows a detail of area 2 of FIG. 1E.
Figure 3:
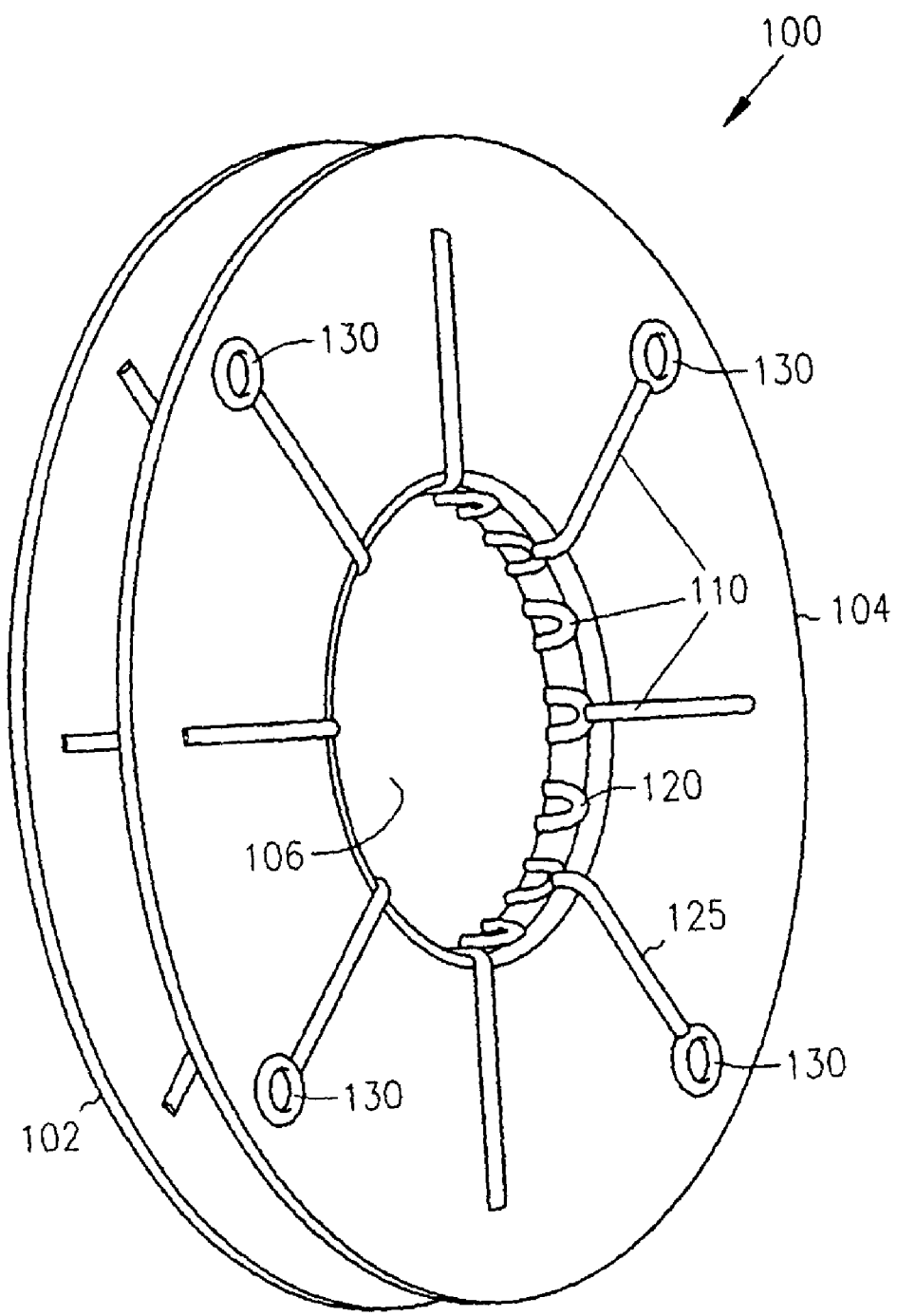
FIG. 3 shows a front perspective view of the vascular occlusion device of FIG. 1A.

FIG. 2 shows one example of a distal end of a rib 125 of device 100. In this example, the end 141 of rib 125 is thinner (approximately 0.01 inches) than the inner portion 143 (approximately 0.025 inches) of the rib. This provides that the periphery area of each flange is a little more flexible and softer than the middle regions. This can help eliminate tissue erosion by the device once it is implanted.

Again, in one embodiment device 100 is molded from a non-metallic material. Such an occlusion device has better tolerance than prior devices and has better long-term stability. Possible materials include: silicone elastomers, polyurethanes, or combinations of the two, and other compatible materials. In one example, device 100 is a one-piece, completely integrated device formed of a single material with ribs 110 being thicker parts of the material. This allows for fast manufacturability since the device can be molded or otherwise formed in a single process. In some embodiments, the ribs are formed of one type of material and the membrane portion from a different type of material.

In one embodiment, the device includes a bio-adsorbable material. Possible bio-adsorbable material include: polyglycolic acid, polydioxanone, polylactic acid, and polycaprolactone, etc. Some embodiments use other bio-degradable and bioabsorbable plastics. Again, in some embodiments, these poly materials can be used to form the device as a single integrated unit formed of a single, moldable material. Using a bioadsorbable material as described above allows the device to slowly be resorbed into the body while the poly material is replaced by tissue. This results in a closed defect and leaves no metallic parts in a body.

FIGS. 8A-10 show a vascular occlusion device 200 according to one embodiment. Device 200 includes a pair of disk members defining a pair of flange members 202 and 204 connected by a central area 206. The skeleton structure 210 of occlusion device 200 includes an appearance of the petals of a flower. The skeleton 210 of device 200 runs across from one side to the other through a central area 206. In this example, skeleton 210 includes rib portions 225 running towards and around the periphery of each flange of the device. Holes 230 are provided similar to holes 130 described above. Again, the central area 206 can be dimensioned to provide a self-centering device by having an outer rim surface 220 to abut the defect. While the disk shape shown is square-shaped, it may be round, oval, rectangular, or any other desirable shape. The thickness of the skeleton is variable and is determined by the occlusive pressures that will force the device from the defect. The thickness of the membrane can be variable. In one example, the membrane portion can be about 0.010 inches or less, with the ribs being about 0.020 inches to 0.025 inches. The membrane in both the flanges can be perforated, and sieve like, to reduce the bulk of the device, so that it can be more easily loaded into a catheter. It would be desirable for the central area to be free of perforations for the shunt to be occluded. In one embodiment, the central area 206 is about 10 mm in diameter and each flange has a diameter of approximately 28 mm.

Device 200 can be constructed of the same material as for device 100 and the above discussion is incorporated herein by reference.

Figure 11C:
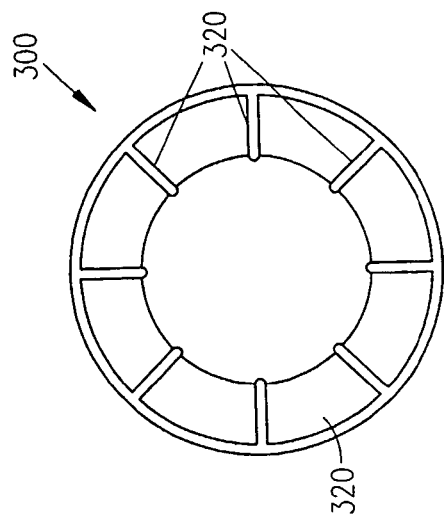
FIGS. 11A-11C show side, top and bottom view of a device according to one embodiment.
Figure 11A:
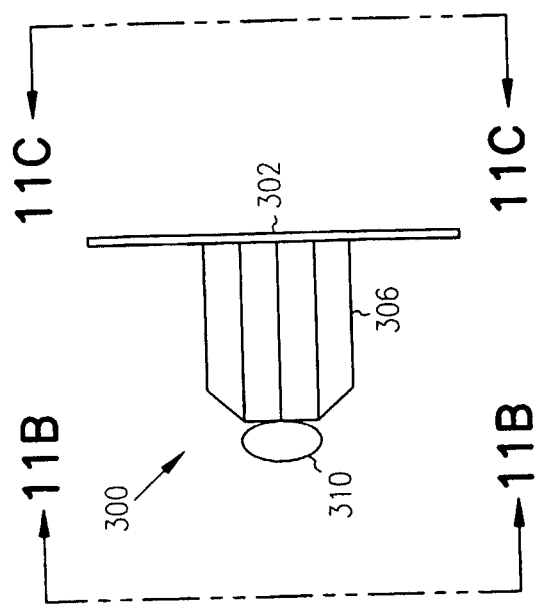
Figure 11B:
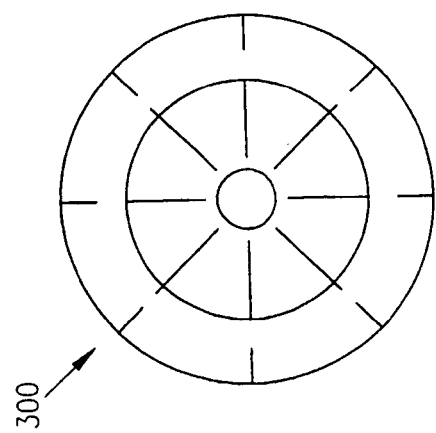

FIGS. 11A-11C show a device 300 for closure of patent ductus arteriosii (PDA), according to one embodiment. Device 300 includes only one disk 302. There is a central tubular area 306 that is sized to fit into the patent ductus arteriosus. The circular ring 310 is for the release mechanism. Device 300 can be loaded into a catheter and this is used to cross the PDA. The circular disk 302 and the tubular section 306 are opened in the aorta and then it is pulled back into the PDA, so that the disk occludes the defect, and the tubular section seated in the PDA, keeps it in place and centered. If required, the device can be drawn back into the catheter for retrieval in case of sub-optimal deployment.

Device 300 can be constructed of the same material as for device 100 and the above discussion is incorporated herein by reference. Device 300 can include ribs 320 extending outwardly along a face of the disk 302. Again, in one embodiment, device 300 can be formed as an integral, one-piece design. For example, device 300 can be molded from a plastic material, such as a bioadsorbable material as discussed above.

FIGS. 12A-13D show a device 400 that can be used to occlude puncture sites in the femoral artery or vein after percutaneous interventions, in accordance with one embodiment. In one example, device 400 includes a bio-adsorbable polymer. It has an intra-vascular member 402 that is rectangular in shape or oval. This is connected by a wide "waist" 404 to the extra-vascular member 406, that leads to a ring 408. One feature of this device is that the waist is designed to be slightly larger than the puncture hole in the artery or vein. For instance, with 6, 8 or 10 French catheter systems, the hole in the vessel can be as large as 1.98, 2.64, or 3.3 mm. The occluder is designed in different sizes so that the waist between the intravascular and extravascular disks are 2, 2.75 or 3.5 mm in diameter. This allows the present device to fit into the hole and tightly occlude it.

Figure 12A:
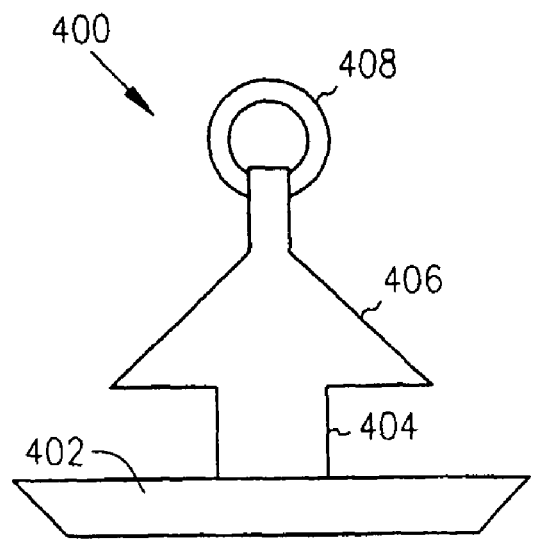
FIG. 12A shows a device in accordance with one embodiment.
Figure 12B:
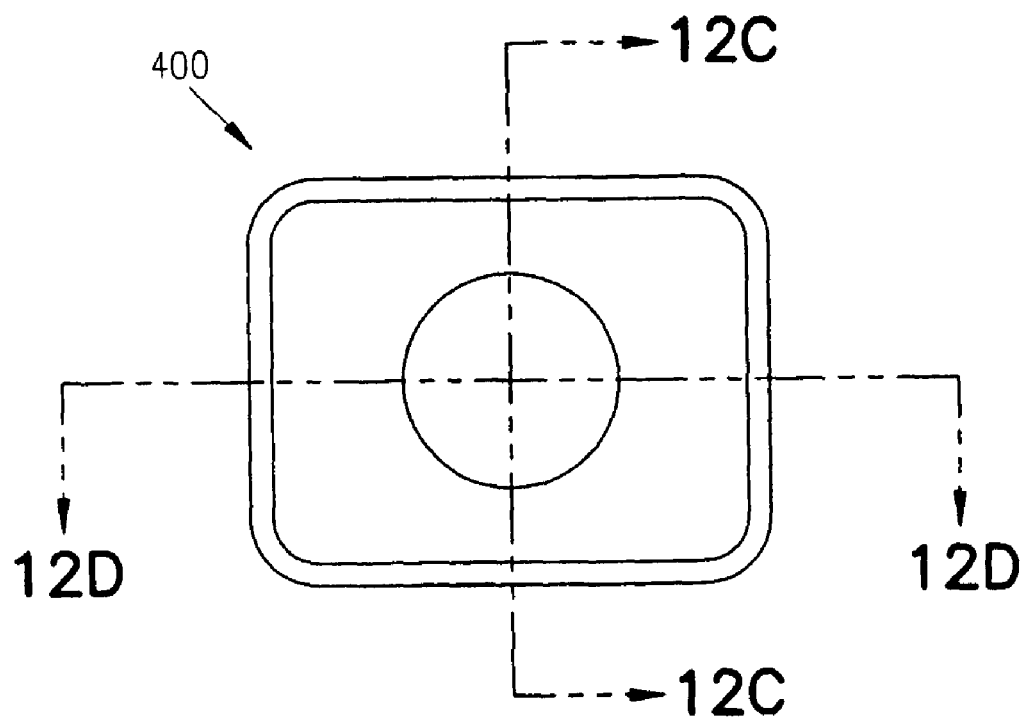
FIG. 12B shows a top view of a portion of the device of FIG. 12A.
Figure 12C:
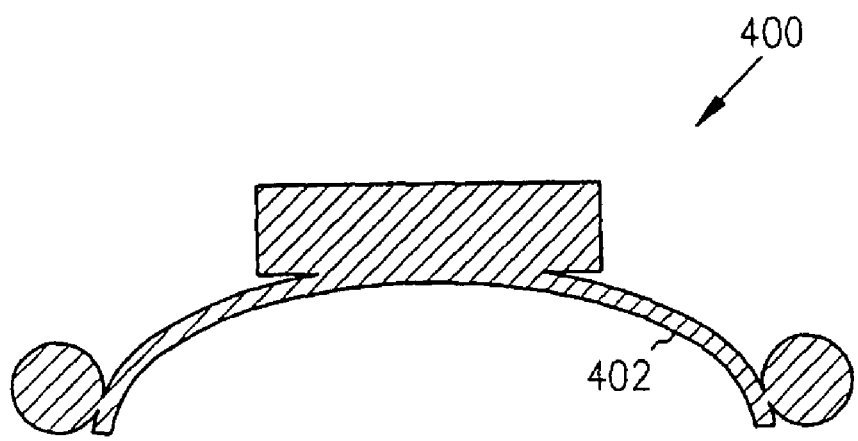
FIG. 12C shows a cross section of line C-C of FIG. 12B.
Figure 12D:
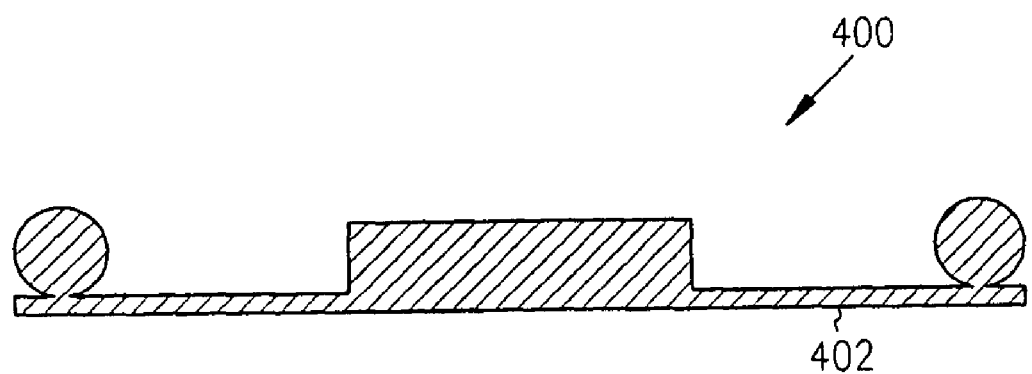
FIG. 12D shows a cross-section of line D-D of FIG. 12B.
Figure 13A:
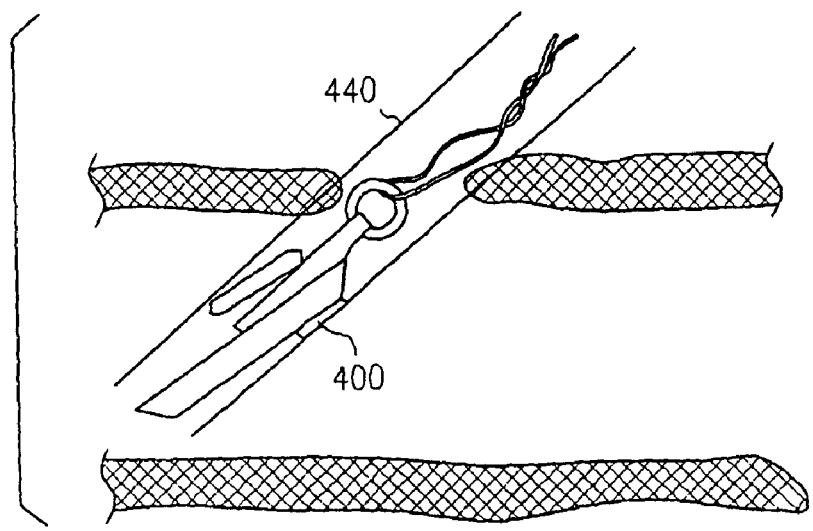
FIGS. 13A-13D show the device of FIG. 12A being deployed in accordance with one embodiment.
Figure 13B:
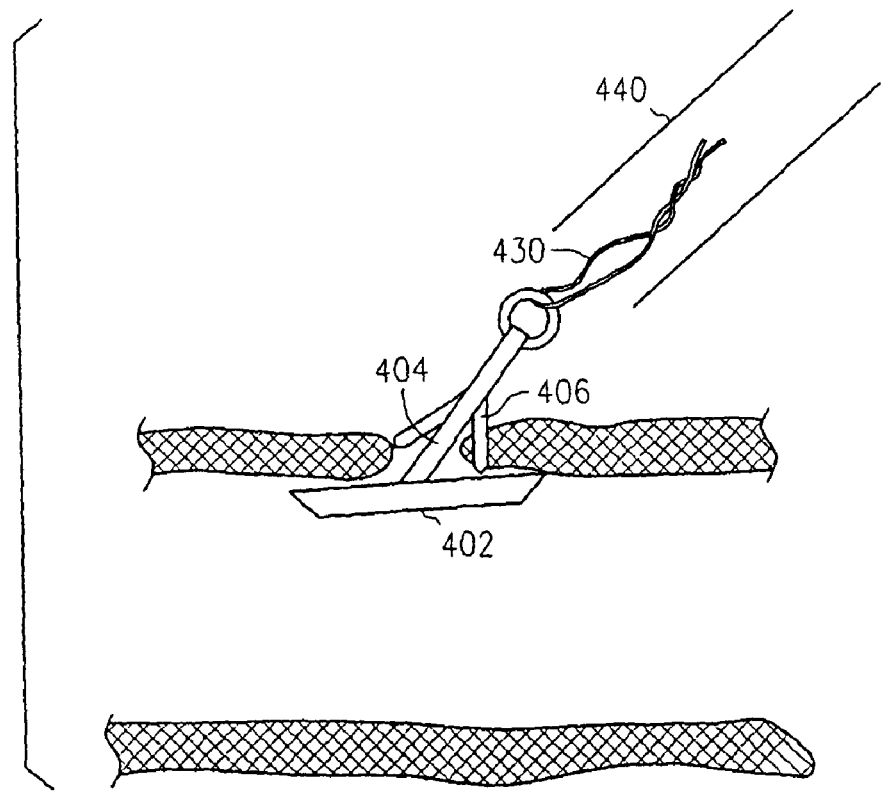
Figure 13C:
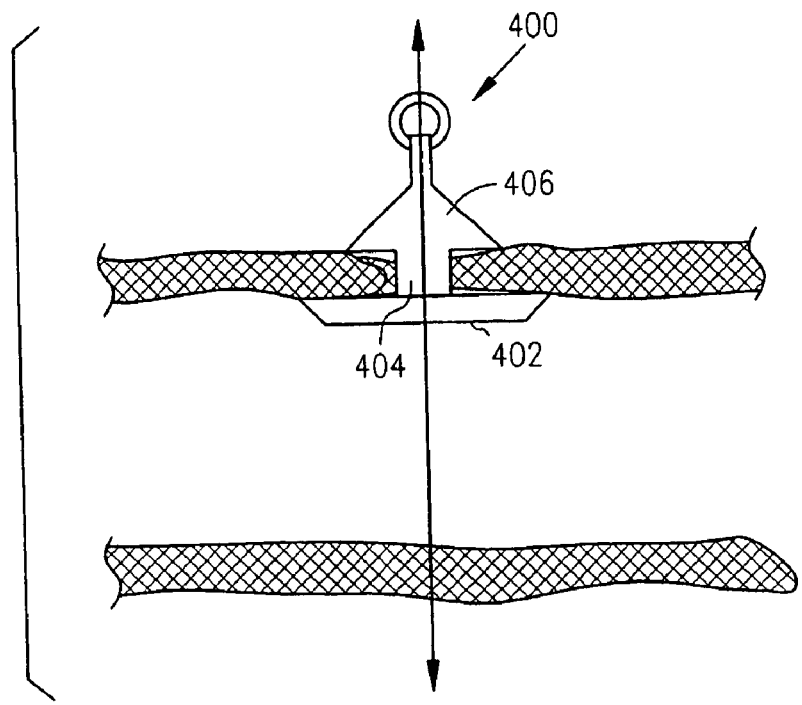
Figure 13D:
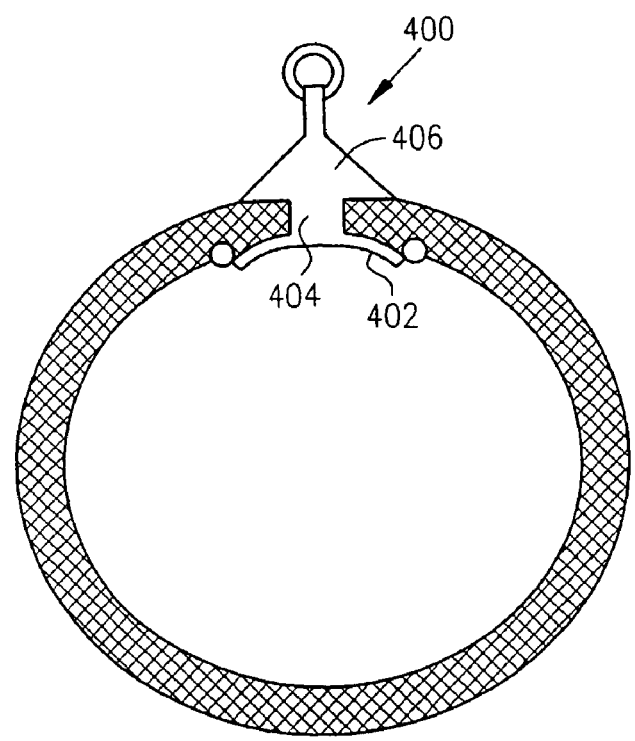

FIGS. 12B-12D show the shape of intra-vascular member 402 according to one embodiment. In this example, member 402 has a rectangle shape of approximately 6 mm by 8 mm, and which is curved to form a partial cylindrical shape. This allows the member to sit flush against an inner surface along the axis of the artery (See FIG. 13D).

The external disk 406 is structured to prevent device 400 from prolapsing back into the artery and producing a total occlusion of the artery. Device 400 can be constructed of the same material as for device 100 and the above discussion is incorporated herein by reference.

FIGS. 13A-13D show one example of device 400 in use. For example, after a percutaneous procedure, an angiogram is obtained to identify the site of puncture, to ensure that it is above the bifurcation of the femoral artery. Device 400 is loaded into its sheath and this is passed through the previous sheath into the common iliac artery. The device is partially extruded until the intravascular disk 402 opens inside the artery. The whole unit is withdrawn, until the intravascular disk is snug against the artery. The device is held in place, using the release device 430, and the sheath 440 is drawn back so that the extravascular disk is opened. The sheaths are drawn back. The "self-centering" mechanism of the device permits the device to tightly occlude the defect. The intravascular disk prevents the device from being blown out by the intra-arterial pressure. Once hemostasis is confirmed, the device is released. It is anticipated that the bioadsorbable polymer would resorb over the course of a few weeks and heal with no foreign bodies remaining in the site.

Moreover, in one or more embodiments discussed above, the material of a device can be modified as necessary to prolong or shorten the resorption period to allow for predictable resorption times.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An occlusion device comprising:
   first and second disk members which are connected together, each of the first and second disk members having a self-expanding, non-metallic structure including a plurality of integral rib members which are flexible so as to be compressible within a catheter and are biased towards an open position to automatically expand the disk members when the disk members are removed from the catheter, wherein one or more of the rib members are thinner towards an outer end of the rib member such that a periphery area of each disk member is more flexible than an inner area of each disk member; and
   a collapsible central rim connecting the first and second disk members together, the collapsible central rim defining a central occluding area located within the central rim that is dimensioned to extend across a diameter of a hole to occlude the hole, wherein the central rim has an outer periphery defining a membrane surface and a sinuous skeleton structure on the membrane surface extending around the outer periphery of the central rim.

2. The occlusion device of claim 1, wherein the occlusion device includes a bioabsorbable material.

3. The occlusion device of claim 2, wherein the bioabsorbable material includes polyglycolic acid.

4. The occlusion device of claim 2, wherein the bioabsorbable material includes polydioxanone.

5. The occlusion device of claim 2, wherein the bioabsorbable material includes polylactic acid.

6. The occlusion device of claim 2, wherein the bioabsorbable material includes polycaprolactone.

7. The occlusion device of claim 1, wherein the sinuous skeleton structure is configured to bias the central rim in an outward direction.

8. The occlusion device of claim 1, wherein each of the plurality of ribs are radially oriented on the first and second disk members.

9. The occlusion device of claim 1, wherein at least a portion of the plurality of ribs define a petal-shaped configuration.

10. The occlusion device of claim 1, wherein the sinuous skeleton structure located around the periphery of the central rim bias the periphery of the central rim against the tissue.

11. The occlusion device of claim 1, further including one or more holes formed in one of the disk members proximate a periphery of the disk member.

12. The occlusion device of claim 11, wherein each of the one or more holes are encircled by a portion of the rib members.

13. The occlusion device of claim 1, wherein the occlusion device is a one-piece integral device.

14. The occlusion device of claim 1, wherein the occlusion device is a one-piece integral device formed of a non-metallic material.

15. An occlusion device comprising:
    a pair of disk members connected together at a central occluding area, wherein each of the pair of disk members includes a membrane flange having integral rib sections, and wherein the integral rib sections each include a plurality of ribs which extend radially along a surface of the membrane flange towards a periphery of the disk members, and one or more holes formed proximate the periphery of one of the disk members, wherein one or more of the ribs are thinner towards an outer end of the rib such that a periphery area of each disk member is more flexible than an inner area of each disk member, and wherein the central occluding area includes a collapsible central rim located around the central occluding area and connecting the first and second disks together in the central occluding area, the collapsible central rim dimensioned to extend across a diameter of a hole so that the central occluding area occludes the hole, and wherein the central rim has an outer periphery defining a membrane surface and a sinuous skeleton structure on the membrane surface extending around the outer periphery of the central rim.

16. The occlusion device of claim 15, wherein each of the disk members are adapted to be self-expanding.

17. The occlusion device of claim 15, wherein the occlusion device includes a bioabsorbable material.

18. The occlusion of claim 15, wherein the sinuous skeleton structure located around the periphery of the central rim biases the periphery of the central rim outward.

19. The occlusion device of claim 15, wherein each of the one or more holes are encircled by a portion of the rib members.

20. An occlusion device comprising:
   first and second flanges which are connected together with a central occluding section located between the first and second flanges, wherein the central occluding section includes a collapsible central rim which is dimensioned to extend across a diameter of a hole in a tissue, and wherein each of the first and second flanges include a self-expanding, non-metallic structure including a membrane with a plurality of integral rib members located along a surface of the membrane and wherein the rib members are flexible so as to be compressible within a catheter and are biased towards an open position to automatically expand the flanges when the flanges are removed from the catheter, wherein one or more of the ribs are thinner towards an outer end of the rib such that a periphery area of each flange is more flexible than an inner area of each flange, and wherein the first and second flanges, the rib members, and the central occluding section are all formed as a one-piece integral unit formed from a bioabsorbable material, and wherein the central rim has an outer periphery defining a membrane surface and a sinuous skeleton structure on the membrane surface extending around the outer periphery of the central rim.

21. The occlusion device of claim 20, wherein the integral rib members extend radially towards a periphery of the flanges.

22. The occlusion device of claim 20, further including one or more holes formed proximate the periphery of one of the flanges.

* * * * *

UNITED STATES PATENT AND TRADEMARK OFFICE
CERTIFICATE OF CORRECTION

PATENT NO. : 8,430,934 B2  
APPLICATION NO. : 10/931937  
DATED : April 30, 2013  
INVENTOR(S) : Gladwin S. Das Page 1 of 2

It is certified that error appears in the above-identified patent and that said Letters Patent is hereby corrected as shown below:

On the Title Page, in column 2, under "Other Publication", line 1, before ""Application", delete "2003-572469,", therefor On the Title Page, in column 2, under "Other Publication", line 2, after "mailed", delete "on", therefor On the Title Page, in column 2, under "Other Publication", line 2, delete "2." and insert --2 pgs.--, therefor On the Title Page, in column 2, under "Other Publication", line 3, delete "No. 2,477,833 ,Notice" and insert --Serial No. 2,477,833, Notice--, therefor On the Title Page, in column 2, under "Other Publication", line 3-4, delete "Mailed on" and insert --mailed--, therefor On the Title Page, in column 2, under "Other Publication", line 6, delete "Filed" and insert --filed--, therefor On the Title Page, in column 2, under "Other Publication", line 6, delete "Office Action Response Filed, 5." and insert --5 pgs.--, therefor In the Specification In column 1, line 25, after "proximate", insert --to--, therefor In column 3, line 6, delete "FIG." and insert --FIGS.--, therefor Signed and Sealed this  
Thirty-first Day of December, 2013

Margaret A. Focarino  
*Commissioner for Patents of the United States Patent and Trademark Office*

CERTIFICATE OF CORRECTION (continued)
U.S. Pat. No. 8,430,934 B2

In the Claims

In column 6, line 45, in Claim 11, after "proximate", insert --to--, therefor

In column 6, line 62-63, in Claim 15, after "proximate", insert --to--, therefor In column 8, line 23, in Claim 22, after "proximate", insert --to--, therefor